US009733185B2

(12) United States Patent
Cao et al.

(10) Patent No.: US 9,733,185 B2
(45) Date of Patent: Aug. 15, 2017

(54) GRADIENT STRUCTURES INTERFACING MICROFLUIDICS AND NANOFLUIDICS, METHODS FOR FABRICATION AND USES THEREOF

(71) Applicant: Princeton University, Princeton, NJ (US)

(72) Inventors: Han Cao, San Diego, CA (US); Jonas O. Tegenfeldt, Lund (SE); Stephen Chou, Princeton, NJ (US); Robert H. Austin, Princeton, NJ (US)

(73) Assignee: Princeton University, Princeton, NJ (US)

( * ) Notice: Subject to any disclaimer, the term of this patent is extended or adjusted under 35 U.S.C. 154(b) by 606 days.

(21) Appl. No.: 13/675,685

(22) Filed: Nov. 13, 2012

(65) Prior Publication Data

US 2014/0030811 A1    Jan. 30, 2014

Related U.S. Application Data

(62) Division of application No. 11/536,178, filed on Sep. 28, 2006, now Pat. No. 8,333,934, which is a division of application No. 10/414,620, filed on Apr. 16, 2003, now Pat. No. 7,217,562.

(60) Provisional application No. 60/373,409, filed on Apr. 16, 2002, provisional application No. 60/419,742, filed on Oct. 18, 2002.

(51) Int. Cl.
| | |
|---|---|
| *G01N 35/02* | (2006.01) |
| *G01N 33/00* | (2006.01) |
| *C12M 1/36* | (2006.01) |
| *C12M 3/00* | (2006.01) |
| *G01N 21/64* | (2006.01) |
| *B01L 3/00* | (2006.01) |
| *B81C 1/00* | (2006.01) |
| *B82Y 30/00* | (2011.01) |
| *G01N 33/487* | (2006.01) |
| *G03F 7/20* | (2006.01) |

(52) U.S. Cl.
CPC .... *G01N 21/6486* (2013.01); *B01L 3/502707* (2013.01); *B01L 3/502746* (2013.01); *B01L 3/502761* (2013.01); *B81C 1/00119* (2013.01); *B82Y 30/00* (2013.01); *G01N 33/48721* (2013.01); *G03F 7/2008* (2013.01); *B01L 3/502715* (2013.01); *B01L 2200/027* (2013.01); *B01L 2200/0663* (2013.01); *B01L 2200/12* (2013.01); *B01L 2300/0654* (2013.01); *B01L 2300/0896* (2013.01); *B01L 2400/0415* (2013.01); *B01L 2400/086* (2013.01); *B81B 2201/058* (2013.01); *B81C 2201/0157* (2013.01); *B81C 2201/0159* (2013.01); *Y10T 436/143333* (2015.01)

(58) Field of Classification Search
None
See application file for complete search history.

(56) References Cited

U.S. PATENT DOCUMENTS

| | | | |
|---|---|---|---|
| 3,973,121 A * | 8/1976 | Fite et al. | 250/292 |
| 4,283,276 A * | 8/1981 | Grant | 209/155 |
| 5,772,905 A | 6/1998 | Chou | |
| 5,867,266 A | 2/1999 | Craighead | |
| 6,083,758 A | 7/2000 | Imperiali et al. | |
| 6,165,688 A | 12/2000 | Celotta et al. | |
| 6,182,733 B1 | 2/2001 | McReynolds | |
| 6,210,896 B1 | 4/2001 | Chan | |
| 6,214,246 B1 | 4/2001 | Craighead | |
| 6,263,286 B1 | 7/2001 | Gilmanshin et al. | |
| 6,304,318 B1 | 10/2001 | Matsumoto | |
| 6,309,580 B1 | 10/2001 | Chou | |
| 6,334,960 B1 | 1/2002 | Wilson et al. | |
| 6,355,420 B1 | 3/2002 | Chan | |
| 6,403,311 B1 | 6/2002 | Chan | |
| 6,406,893 B1 | 6/2002 | Knapp et al. | |
| 6,438,279 B1 | 8/2002 | Craighead et al. | |
| 6,440,645 B1 | 8/2002 | Yon-Hin et al. | |
| 6,440,662 B1 | 8/2002 | Gerwen et al. | |
| 6,482,742 B1 | 11/2002 | Chou | |

(Continued)

FOREIGN PATENT DOCUMENTS

| | | |
|---|---|---|
| WO | WO 00/09757 | 2/2000 |
| WO | WO 01/13088 | 2/2001 |

(Continued)

OTHER PUBLICATIONS

"Human Genome Project," Wikipedia.com, accessed Jun. 7, 2013.*

(Continued)

*Primary Examiner* — Bradley L Sisson

(74) *Attorney, Agent, or Firm* — Riverside Law LLP

(57) ABSTRACT

The present invention relates to a device for interfacing nanofluidic and microfluidic components suitable for use in performing high throughput macromolecular analysis. Diffraction gradient lithography (DGL) is used to form a gradient interface between a microfluidic area and a nanofluidic area. The gradient interface area reduces the local entropic barrier to nanochannels formed in the nanofluidic area. In one embodiment, the gradient interface area is formed of lateral spatial gradient structures for narrowing the cross section of a value from the micron to the nanometer length scale. In another embodiment, the gradient interface area is formed of a vertical sloped gradient structure. Additionally, the gradient structure can provide both a lateral and vertical gradient.

20 Claims, 16 Drawing Sheets

(56) References Cited

U.S. PATENT DOCUMENTS

| | | | |
|---|---|---|---|
| 6,515,751 | B1 | 2/2003 | Craighead et al. |
| 6,518,189 | B1 | 2/2003 | Chou |
| 6,685,841 | B2 | 2/2004 | Lopez et al. |
| 6,755,621 | B2 | 6/2004 | Lopez et al. |
| 7,217,562 | B2 | 5/2007 | Cao et al. |
| 7,670,770 | B2 * | 3/2010 | Chou et al. .................. 435/6.12 |
| 2001/0014850 | A1 | 8/2001 | Gilmanshin et al. |
| 2001/0045357 | A1 | 11/2001 | Broadley et al. |
| 2002/0015149 | A1 | 2/2002 | Rahbar-Dehghan et al. |
| 2002/0028451 | A1 | 3/2002 | Abbott et al. |
| 2002/0039737 | A1 | 4/2002 | Chan et al. |
| 2002/0042027 | A1 | 4/2002 | Chou et al. |
| 2002/0061529 | A1 | 5/2002 | Bridgham et al. |
| 2002/0072243 | A1 | 6/2002 | Craighead et al. |
| 2002/0081744 | A1 | 6/2002 | Chan et al. |
| 2002/0132482 | A1 | 9/2002 | Chou |
| 2002/0160356 | A1 | 10/2002 | Craighead et al. |
| 2002/0160365 | A1 | 10/2002 | O'Brien |
| 2002/0167117 | A1 | 11/2002 | Chou |
| 2003/0012657 | A1 | 1/2003 | Marr et al. |
| 2003/0012866 | A1 | 1/2003 | Harnett et al. |
| 2003/0034329 | A1 | 2/2003 | Chou |
| 2003/0080471 | A1 | 5/2003 | Chou |
| 2003/0080472 | A1 | 5/2003 | Chou |
| 2003/0170995 | A1 | 9/2003 | Chou |
| 2003/0170996 | A1 | 9/2003 | Chou |
| 2004/0197843 | A1 | 10/2004 | Chou et al. |
| 2005/0023156 | A1 | 2/2005 | Ramsey et al. |

FOREIGN PATENT DOCUMENTS

| | | |
|---|---|---|
| WO | WO 01/37958 | 5/2001 |
| WO | WO 01/40869 | 6/2001 |
| WO | WO 02/07199 | 1/2002 |
| WO | WO 03/010289 | 2/2003 |
| WO | WO 03/079416 | 9/2003 |
| WO | WO 03/106693 | 12/2003 |

OTHER PUBLICATIONS

"List of sequenced bacterial genomes," Wikipedia.com; accessed Jan. 24, 2014.*
"How many species of bacteria are there?" WiseGeek.com, accessed Jan. 21, 2014.*
("Human Genome Project," Wikipedia.com, accessed Jun. 7, 2013.*
"List of sequenced bacterial genomes" (Wikipedia.com; accessed Jan. 24, 2014).*
"Sequenced plant genomes," GenomeEvolution.org; accessed Feb. 23, 2014.*
Dumbravescu, "Smooth 3-D Shaping of Thick Resists by Means of Gray Tone Lithography" Semiconductor Conference, 1999, CAS '99 Proceedings, 1999, International Sinala, Romania, Oct. 5-9, 1999, IEEE, US, Piscataway, NJ, Oct. 5, 1999, vol. 1, 217-220.
Henke et al., "Simulation and Experimental Study of Graytone Lithography for the Fabrication of Arbitrarily Shaped Surfaces" Proceeding of the Workshop on Micro Electro Mechanical Systems (Mems). Oiso, Jan. 25-28, 1994, New York, IEEE, US, vol. Workshop 7, Jan. 25, 1994, 205-210.
Thornell et al., "Microprocessing At the Fingertips" Journal of Micromechanics & Microengineering, Institute of Physics Publishing, Bristol, GB, 8(4), Dec. 1, 1998, 251-262.
Akeson, M., et al., "Microsecond time-scale discrimination among polycyctidylic acid, polyadenylic acid, and polyuridylic acid as homopolymers or as segments within single RNA molecules," Biophysical J., 1999, 77, 3227-3233.
Austin, R.H., et al., "Scanning the controls: genomics and nanotechnology," IEEE Trans. On Nanotechnology, 2002, 1(1), 12-18.
Bakajin, O., "Separation of 100-kilobase DNA molecules in 10 seconds," Anal. Chem., 2001, 73, 6053-6056.
Ball, P., "DNA combed into nanochannels," NPG Nature Publishing Group, wysiwyg://6/http://www.nature.com, 2002, downloaded Nov. 27, 2002, 2 pages.

Bates, M., et al., "Dynamics of DNA molecules in a membrane channel probed by active control techniques," Biophysical J., 2003, 84, 2366-2372.
Bhusari, D., et al., "Fabrication of air-channel structures for microfluidic, microelectromechanical, and microelectronic applications," J. of Microelectromech. Syst., 2001, 10(3), 400-408.
Braslaysky, I., et al., "Sequence information can be obtained from single DNA molecules," PNAS, 2003, 100(7), 3960-3964.
Cao, H., et al., "Fabrication of 10 nm enclosed nanofluidic channels," Applied Physics Letters, 2002, 81(1), 174-176.
Cao, H., et al., "Gradient nanostructures for interfacing microfluidics and nanofluidics," Applied Physics Letters, 2002, 81(16), 3058-3060.
Cao, H., "Sensors and Sensitivity," Innovation, The Princeton Journal of Science and Technology, about late Fall, 2002, 28-31.
Chou, H.-P., et al., "A microfabricated device for sizing and sorting DNA molecules," Proc. Nat. Acad. Sci. USA, 1999, 96, 11-13.
Chou, C.-F., et al, "Sorting by diffusion: an asymmetric obstacle course for continuous molecular separation," PNAS, 1999, 96(24), 13762-13765.
Chou, S.Y., "Imprint lithography with 25-nanometer resolution," Science, 1996, 272, 85-87.
Gerstner, E., "Put a lid on it!," NPG Publishing Group, wysiwyg://12/http://www.nature.com, 2002, downloaded Jul. 4, 2002, 2 pages.
Han, J., et al., "Separation of long DNA molecules in a microfabricated entropic trap array," Science, 2000, 288, 1026-1029.
Han, J., et al., "Characterization and optimization of an entropic trap for DNA separation," Analytical Chem., 2002, 74, 394-401.
Han, J., et al., "From microfluidics to nanofluidics: DNA separation using nanofluidic entropic trap array device," Proceedings of SPIE, 2000, vol. 4177, 42-48.
Harnett, C.K., et al., "Heat-depolymerizable polycarbonates as electron beam patternable sacrificial layers for nanofluidics," J. Vac. Sci. Technol. B, Nov./Dec. 2001, 19(6), 2842-2845.
Henrickson, S.E., et al., "Driven DNA transport into an asymmetric nanometer-scale pore," Physical Review Letters, 2000, 85(14), 3057-3060.
Ju, S.-P., et al., "Molecular dynamics simulation of sputter trench-filling morphology in damascene process," J. Vac. Sci. Technol. B, May/Jun. 2002, 20(3), 946-955.
Kalaugher, L., "Diffraction gradient lithography aids nanofluidics," IOP Publishers Nanotechnolology, http://nanotechweb.org., 2002, downloaded Oct. 22, 2003, 2 pages.
Kasianowicz, J.J., et al., "Characterization of individual polynucleotide molecules using a membrane channel," Proc. Natl. Acad. Sci. USA, 1996, 93, 13770-13773.
Li, M., et al., "Fabrication of circular optical structures with a 20 nm minimum feature size using nanoimprint lithography," Applied Physics Letts., 2000, 76(6), 673-675.
Li, J., et al., "Ion-beam sculpting at nanometer length scales," Nature, 2001, 412, 166-169.
Li, W., et al., "Sacrificial polymers for nanofluidic channels in biological applications," Nanotechnology, 2003, 14, 578-583.
Mason, J., "Princeton builds tiniest tunnel, reveals nanostamping process," Smalltimes, www.smalltimes.com, download dated Oct. 22, 2003, 2 pages.
Masuda, H., et al., "Highly ordered nanochannel-array architecture in anodic alumina," Am. Inst. Of Physics, 1997, 2770-2772.
Meller, A., et al., "Single molecule measurements of DNA transport through a nanopore," Electrophoresis, 2002, 23, 2583-2591.
Meller, A., et al., "Voltage-driven DNA translocations through a nanopore," Am. Physic. Soc., 2001, 86(15), 3435-3438.
Meller, A., "Dynamics of polynucleotide transport through nanometer-scale pores," J. Phys. Condens. Matter, 2003, 15, R581-R607.
Meller, A., "Rapid nanopore discrimination between single polynucleotide molecules," PNAS, 2000, 97(3), 1079-1084.
Quake, S.R., et al., "From micro- to nanofabrication with soft materials," Science, 2000, 290, 1536-1540.
Riordan, T., "Patents: An obsession with DNA and the human genome leads to development of a technology," New York Times, Mar. 18, 2002, 3 pages.

(56) References Cited

OTHER PUBLICATIONS

Schultz, S., "Discovery could lead to faster, smaller, cheaper computer chips," Princeton University, http://www.princeton.edu, 2002, downloaded Oct. 22, 2003, 2 pages.
Soares, L.L., et al., "Fabrication of dielectric hollow submicrometric pipes," J. Vac. Sci. Technol. B, 2000, 713-716.
Stern, M.B., et al., "Nanochannel fabrication for chemical sensors," J. Vac. Sci. Technol. B, Nov./Dec. 1997, 15(6), 2887-2891.
Stjernstrom, M., et al., "Method for fabrication of microfluidic systems in glass," J. Micromech. and Microeng., 1998, 8, 33-38.
Tan, H., et al., "Roller nanoimprint lithography," J. Vac. Sci. Technol. B, 1998, 16(6), 3926-3928.
"The personal genome sequencer," Technology Review, 2002, 76-79.
Vercoutere, W., et al., "Rapid discrimination among individual DNA hairpin molecules at single-nucleotide resolution using an ion channel," Nature Biotechnology, 2001, 19, 248-252.
www.usgenomics.com, "U.S. genomics awarded patent using fluorophores in direct, linear DNA analysis," U.S. Genomics, 2001, downloaded Mar. 11, 2004, 2 pages.
www.usgenomics.com, "U.S. genomics awarded pioneering patent for direct, linear analysis of DNA," U.S. Genomics, 2002, downloaded Mar. 11, 2004, 2 pages.
www.economist.com, "Stamping on tradition," Science and Technology, 2002, downloaded Jul. 19, 2002, 3 pages.
www.uic.edu, "Mechanical (and statistical-mechanical) properties of biofilaments," Jul. 19, 2002, 13 pages.
www.physics.ucsb.edu, "AFM of single-stranded RNA, triple-stranded DNA and helix turns," Jul. 19, 2002, 2 pages.
www.ee.princeton.edu, "Various pages downloaded from ww.ee.princetonedu/.about.chouweb," on Jul. 19, 2002, 23 pages.
Yu, Z., et al., "Nanoscale GaAs metal-semiconductor-metal photodetectors fabricated using nanoimprint lithography," Applied Physics Letts., 1999, 74(16), 2381-2383.
"Nanochannel Tech Offers Promise for Cheap, Quick DNA Analysis Chips", GenomeWeb.com-BioArray News, the Global Weekly of Biochips & Microarrays, http://www.bioarraynews.com/articles/view.asp?Article=20027216514, Jul. 8, 2002 (Included as Exhibit G in the Declaration of Dr. Han Cao under 37 C.F.R. 1.132, dated Sep. 6, 2005).
Austin, M., et al., "Fabrication of nanocontacts for molecular devices using nanoimprint lithography," J. Vac. Sci. Technol. B, 2002, 20(2), 665-667.
Austin, M.D., "Fabrication of a molecular self-assembled monolayer diode using nanoimprint lithography," Nano Letters, 2003, 3(12), 1687-1690.
Austin, M.D., et al., "Fabrication of 70nm channel length polymer organic thin-film transistors using nanoimprint lithography," Applied Physics Letts., 2002, 81(23), 4431-4433.
Cao, H., "Gradient structures interfacing microfluidics, methods for fabrication and uses thereof," U.S. Appl. No. 10/414,620, Apr. 16, 2003, 1-41.
Chou, S.Y., "Patterned magnetic nanostructures and quantized magnetic disks," Proceedings of the IEEE, 1997, 85(4), 652-671.
Chou, S.Y., et al., "Ultrafast and direct imprint of nanostructures in silicon," Nature, 2002, 417, 835-837.
Chou, S.Y., "Imprint lithography with sub-10 nm feature size and high throughput," Microelectronic Eng., 1997, 35, 237-240.
Cui, B., et al., "Perpendicular quantized magnetic disks with 45 Gbits on a 4.times.4 cm.sup.2 area," J. of Applied Physics, 1999, 85(8), 5534-5536.
Guo, L., et al., "Nanoscale silicon field effect transistors fabricated using imprint lithography," Appl. Phys. Lett., 1997, 71(13), 1881-1883.
Kong, L., et al., "Fabrication, writing, and reading of 10 Gbits/in.sup.2 longitudinal quantized magnetic disks with a switching field over 1000 Oe," Jpn. J. Appl. Phys., 1998, 37, 5973-5975.
Kong, L., et al., "Writing and reading 7.5 Gbits/in.sup.2 longitudinal quantized magnetic disk using magnetic force microscope tips," IEEE Transactions on Magentics, 1997, 33(5), 3019-3021.
Kong, L., "Magnetotransport and domain structures in nanoscale NiFe/Cu/Co spin valve," J. of Applied Physics, 1999, 85(8), 5492-5494.
Krauss, P.R., et al., "Nano-compact disks with 400 Gbit/in.sup.2 storage density fabricated using nanoimprint lithography and read with proximal probe," Appl. Phys. Lett., 1997, 71(21), 3174-3176.
Krauss, P.R., et al., "Fabrication of planar quantum magnetic disk structure using electron beam lithography, reactive ion etching, and chemical mechanical polishing," J. Vac. Sci. Technol. B, 1995, 13(6), 2850-2852.
Li, M., et al., "Direct three-dimensional patterning using nanoimprint lithography," Applied Physics Letts., 2001, 78(21), 3322-3324.
Li, M., et al., "Pattern transfer fidelity of nanoimprint lithography on six-inch wafers," Nanotechnology, 2003, 14, 33-36.
Li, M., et al., "Large area direct nanoimprinting of SiO.sub.2-TiO.sub.2 gel gratings for optical applications," J. Vac. Sci. Tchnol. B, 2003, 21(2), 660-663.
Perry, J.L., et al., "Review of fabrication of nanochannels for single phase liquid flow," Proceedings of ICMM, 2005, 1-8.
Schultz, S., "Accidental discovery—New technique coaxes structures to assemble themselves," Princeton University, downloaded Sep. 30, 2005, http://www.princeton.edu/.about.seasweb/eqnews/spring00/feature2.html, 4 pages.
Stern, M.B., et al., "Nanochannel fabrication for chemical sensors," J. Vac. Sci. Technol. B, 1997, 15(6), 2887-2891.
Strum, J.C., "Multidisciplinary development of platforms for protein identification, expression and control at the single cell level in the post-genomics era," Princeton University, downloaded Sep. 30, 2005, http://www.darpa.mil/dso/thrust/biosci/bim/princeton.html, 4 pages.
Sun, X., et al., "Multilayer resist methods for nanoimprint lithography on nonflat surfaces," J. Vac. Sci. Technol. B, 1998, 16(6), 3922-3925.
Wang, J., et al., "Direct nanoimprint of submicron organic light-emitting structures," Applied Physics Letts., 1999, 75(18), 2767-2769.
Wang, J., et al., "Molecular alignment in submicron patterned polymer matrix using nanoimprint lithography," Applied Physics Letts., 2000, 77(2), 166-168.
Wang, J., et al., "Fabrication of a new broadband waveguide polarizer with a double-layer 190 nm period metal-gratings using nanoimprint lithography," J. Vac. Sci. Technol. B, 1999, 17(6), 2957-2960.
Wu, W., et al., "Large area high density quantized magnetic disks fabricated using nanoimprint lithography," J. Vac. Sci. Technol. B, 1998, 16(6), 3825-3829.
Wu, W., et al., "Room-temperature Si single-electron memory fabricated by nanoimprint lithography," Applied Physics Letts., 2003, 83(11), 2268-2270.
Xia, Q., et al., "Ultrafast patterning of nanostructures in polymers using laser assisted nanoimprint lithography," Applied Physics Letts., 2003, 83(21), 4417-4419.
Yu, Z., et al., "Fabrication of nanoscale gratings with reduced line edge roughness using nanoimprint lithography," J. Vac. Sci. Technol. B, 2003, 21(5), 2089-2092.
Yu, Z., et al., "Fabrication of large area subwavelength antireflection structures on Si using trilayer resist nanoimprint lithography and liftoff," J. Vac. Sci. Technol. B, 2003, 21(6), 2874-2877.
Zhang, W., et al., Multilevel nanoimprint lithography with submicron alignment over 4 in. Si wafers, Applied Physics Letts., 2001, 79(6), 845-847.
Zhang, W., et al., Fabrication of 60-nm transistors on 4-in. wafer using nanoimprint at all lithography levels, Applied Physics Letts., 2003, 83(8), 1632-1634.
Cao, H. et al., "Fabrication of 10 nm Enclosed Nanofluidic Channels", Applied Physics Letters, Jul. 2002, 81(1), 174-176, Listed as Exhibit H in Declaration of Dr Cao.
Chou, S.Y. et al., "Imprint of Sub-25 nm Vias and Trenches in Polymers", Appl. Phys. Lett., 1995, 67(21), 3114-3116, Listed as Exhibit C in Declaration of Dr. Cao.

(56) References Cited

OTHER PUBLICATIONS

Chou, S.Y. et al., "Imprint Lithography with 25-Nanometer Resolution", Science, 1996, 272(5258), 85-87, Listed as Exhibit D in Declaration of Dr. Cao.

Harrison, C. et al., "Lithography with a Mask of Block Copolymer Microstructures", J. Vac. Sci. Technol. B., Mar./Apr. 1998, 16(2), 544-552, Listed as Exhibit F in Declaration of Dr. Cao.

Hamley, I.W., "Structure and Flow Behaviour of Block Copolymers", Journal of Physics: Condensed Matter, 2001, 13, R643-R671.

Morkved, T.L. et al., "Local Control of Microdoniain Orientation in Diblock Copolymer thin Films with Electric Fields", Science, 1996, 273(5277), 931-933.

Yu, Z. et al., "Fabrication of Large Area 100 nm Pitch Grating by Spatial Frequency Doubling and Nanoimprint for Subwavelength Optical Applications", J. Vac. Sci. Technol B, Nov./Dec. 2001, 19(6), 2816-2819, Listed as Exhibit G in Declaration of Dr Cao.

Huang, E. et al., "Nanodomain Control in Copolymer Thin Films", Nature, 1998, 395, 757-758.

Yu, Z.N. et al., Reflective Polarizer Based on a Stacked Double-Layer Subwavelength Metal Grating Structure Fabricated Using Nanoimprint Lithography, Applied Phys. Lett., 2000, 77(7), 927, Listed as Exhibit B in Declaration of Dr. Cao.

Stikeman, A., "Makes the Diagnosis, Want to Detect a Single Anthrax Spore? A Telltale Cancer Protein? The Convergence of Nanoelectronics and Biology is Producing Biosensors of Exquisite Sensitivity", Technology Review, May 2002, 61-66.

Turner, S.W.P., et al., "Confinement-Induced Entropic Recoil of Single DNA Molecules in a Nanofluidic Structure", Physical Review Letters, Mar. 2002, vol. 88.

Foquet, M., et al., "DNA Fragment Sizing by Single Molecule Detection in Submicrometer-Sized Closed Fluidic Channels", Analytical Chemistry, Accepted Dec. 2001.

Turner, S.W., et al., "Monolithic Nanofluid Sieving Structures or DNA Manipulation", J. Vac. Sci. Technol. B. 16(6), Nov./Dec. 1998, pp. 3835-3840.

Tegenfeldt, J., et al., "Near-Field Scanner for Moving Molecules", Physical Review Letters, vol. 86, No. 7, Feb. 12, 2001 pp. 1378-1381.

\* cited by examiner

Steep entropy barrier

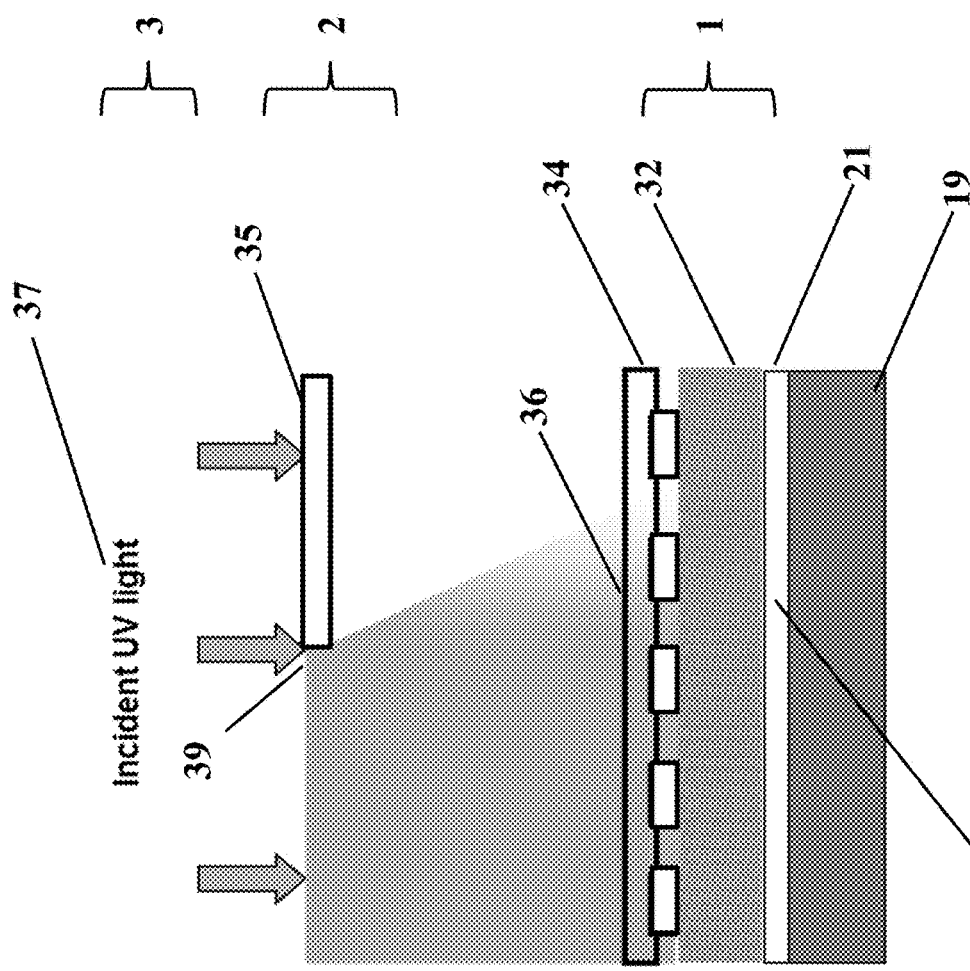

GRADIENT STRUCTURES INTERFACING MICROFLUIDICS AND NANOFLUIDICS, METHODS FOR FABRICATION AND USES THEREOF

CROSS-REFERENCE TO RELATED APPLICATIONS

The present application is a divisional application of U.S. patent application Ser. No. 11/536,178, filed Sep. 28, 2006, now U.S. Pat. No. 8,333,934, which is a divisional application of U.S. patent application Ser. No. 10/414,620, filed on Apr. 16, 2003, now U.S. Pat. No. 7,217,562, which claims the benefit of priority under 35 U.S.C. §119(e) to U.S. Provisional Application No. 60/373,409, filed on Apr. 16, 2002 and U.S. Provisional Application No. 60/419,742, filed Oct. 18, 2002, each of which applications are incorporated by reference herein in their entirety.

STATEMENT OF GOVERNMENT SUPPORT

This invention was made with government support under DARPA Grant Number MDA972-00-1-0031. The government has certain rights in the invention.

BACKGROUND OF THE INVENTION

1. Field of the Invention

The present invention relates to bionanotechnology and in particular to a method of fabricating a hybrid microfluidic/nanofluidic device having a gradient structure formed by a modified photolithography technique at the interface between microfluidic and nanofluidic portions of the device and uses thereof.

2. Description of the Related Art

Nanotechnology, electronics and biology are combined in the newly emerging field of bionanotechnology. Nanofabrication of extremely small fluidic structures, such as channels, can be used in bionanotechnology for the direct manipulation and analysis of biomolecules, such as DNA, and proteins at single molecule resolution. For example, the channels can be used for stretching genomic DNA and scanning for medically relevant genetic or epigenetic markers. New insights of understanding the confinement-mediated entropic behavior of biopolymers in ultra-small nanoscale fluidics have just started to emerge.

On the nanometer scale, DNA is a stiff molecule. The stiffness of the molecule is described by a parameter called the persistence length. Despite the relative stiffness of DNA for sufficiently long molecules, it tends to form a disordered tangle of compact random coils in free solution. The conformation of a polymer in free solution has been referred to as a spherical "blob" by the polymer dynamics community. The size of the blob depends on the length of the DNA molecule and the persistence length.

It has been described that in order to uniformly stretch chain-like long DNA, dimensions of nanofluidic structures should be near, in the vicinity of or smaller than the persistence length of double stranded DNA of about 50 nm to about 70 nm. Arrays of up to half millions of nanochannels fabricated over a 100 mm wafer using nanoimprinting lithography (NIL) with sealed channels having a cross section as small as 10 nm by 50 nm to stretch, align and analyze long genomic DNA in a highly parallel fashion, and the resulting have been described in Cao H., Wang J., Tegenfeldt P., Austin R. H., Chen E., Wei W. and Chou S. Y., Fabrication of 10 nm Enclosed Nanofluidic Channels (2002) Applied Physics Letters, Vol. 81, No. 1, pp 174. It is challenging to efficiently move long DNA arranged as a blob into the small channels, since it is energetically unfavorable for long biopolymers to spontaneously elongate and enter nanochannels directly from the environment due to the large free energy needed to overcome negative entropy change, as illustrated in FIGS. 1A-1B. For example, a double stranded T4 phage DNA molecule with a length of 169 kilobases will form a Gaussian coil with a radius of gyration (Rg= $(L\rho/6)^{1/2}$, where L is the length and .rho. the persistence length of the DNA), approximately 700 nm in aqueous buffer solution which is many times the width of the opening of the nanochannels. Consequently, problems such as DNA clogging at the junction of nano- and macro-environment have arisen and undermine the performance of conventional nanofluidic devices.

U.S. Patent Application Publication No. 2002/0160365 describes a method for separation of long strands of DNA by length by forcing the molecules to traverse a boundary between a low-force energy region and a high-force energy region. The high-force energy region is a diverse pillar region. The low-force energy region is a larger chamber formed adjacent the high-force energy region.

U.S. Patent Application Publication No. 2002/0072243 describes fabrication techniques using a pattern of sacrificial and permanent layers to define the interior geometry of a fluidic device. A pattern for a fluidic device having microchannels and an array of retarding obstacles is defined in a resist layer. The pattern is produced using lithographic techniques. For electron beam lithography and for deep structures made with photolithography, a hard pattern mask is required to assist in pattern transfer. An inlet chamber, outlet chamber, inlet microchannel, outlet chamber and an array of holes is formed in a sacrificial layer. A ceiling layer is deposited to cover the sacrificial layer. The ceiling layer enters the holes to form closely spaced pillars. The sacrificial layer is removed to form microchannels between the floor and ceiling layers. The pillars act as a sieve or an artificial gel filter for fluid flowing through the system. Steps needed in removing the sacrificial materials, such as heating the substrate up to 200-400° C., limits the use of certain materials. Electron beam lithography has the flexibility to write different patterns, but has low throughput and high manufacturing costs.

It is desirable to provide an improved structure interfacing between microfluidic and nanofluidic components of a device for reducing the local entropic barrier to nanochannel entry and an improved method for fabrication thereof.

SUMMARY OF THE INVENTION

The present invention relates to a device for interfacing nanofluidic and microfluidic components suitable for use in performing high throughput i.e., macromolecular analysis. Diffraction gradient lithography (DGL) is used to form a gradient interface between a microfluidic area and a nanofluidic area. The gradient interface area reduces the local entropic barrier to nanochannels formed in the nanofluidic area.

In one embodiment, the gradient interface area is formed of lateral spatial gradient structures for narrowing the cross section of a value from the micron to the nanometer length scale. In another embodiment, the gradient interface area is formed of a vertical sloped gradient structure. Additionally, the gradient structure can provide both a lateral and vertical gradient. The gradient structures can be used to squeeze and funnel biomolecules into a small nanofluidic area.

In one aspect of the invention, a method for fabricating a fluidic device by diffraction gradient lithography comprises forming a nanofluidic area on a substrate, forming a microfluidic area on the substrate and forming a gradient interface area between the nanofluidic area and the microfluidic area. The gradient interface area can be formed by using a blocking mask positioned above a photo mask and/or photoresist during photolithography. The edge of the blocking mask provides diffraction to cast a gradient light intensity on the photoresist. In another embodiment, a system is provided for fabricating the fluidic device.

In one aspect of the invention, the nanofluidic components comprise nanoscale fluidic structures. The nanofluidic structures can include nanopillars, nanopores and nanochannel arrays.

In another aspect of the invention, a fluidic device is formed of a gradient interface between a nanofluidic area and a microfluidic area, at least one sample reservoir in fluid communication with the microfluidic area, the sample reservoir capable of releasing a fluid and at least one waste reservoir in fluid communication with the nanofluidic area, the waste reservoir capable of receiving a fluid. In another aspect a system for carrying out analysis is provided including a fluidic device is formed of a gradient interface between a nanofluidic area and a microfluidic area, at least one sample reservoir in fluid communication with the microfluidic area, the sample at least one reservoir capable of releasing a fluid and at least one waste reservoir in fluid communication with at least one of the channels the waste reservoir capable of receiving a fluid, signal acquisition and a data processor. The signal can be a photon, electrical current/impedance measurement or change in measurements. The fluidic device can be used in MEMS and NEMS devices.

In another embodiment, methods for analyzing at least one macromolecule are provided which, for example, include the steps of: providing a fluidic device formed of a gradient interface between a nanofluidic area and a microfluidic area, at least one sample reservoir in fluid communication with the microfluidic area, the at least one sample reservoir capable of releasing a fluid and at least one waste reservoir in fluid communication with the nanofluidic area, the waste reservoir capable of receiving a fluid, transporting at least one macromolecule from the microfluidic area to the nanofluidic area to elongate the at least one macromolecule, detecting at least one signal transmitted from the at least one macromolecule and correlating the detected signal to at least one property of the macromolecule.

Cartridges including a nanofluidic chip in accordance with this invention are also disclosed herein. Such cartridges are capable of being inserted into, used with and removed from a system such as those shown herein. Cartridges useful with analytical systems other than the systems of the present invention are also comprehended by this invention.

The invention will be more fully described by reference to the following drawings.

BRIEF DESCRIPTION OF THE DRAWINGS

FIGS. 4A-4D diagrammatically illustrate a process incorporating diffraction gradient lithography (DGL) to fabricate a micropost array and interface gradient structure.

DETAILED DESCRIPTION

Figure 1A:
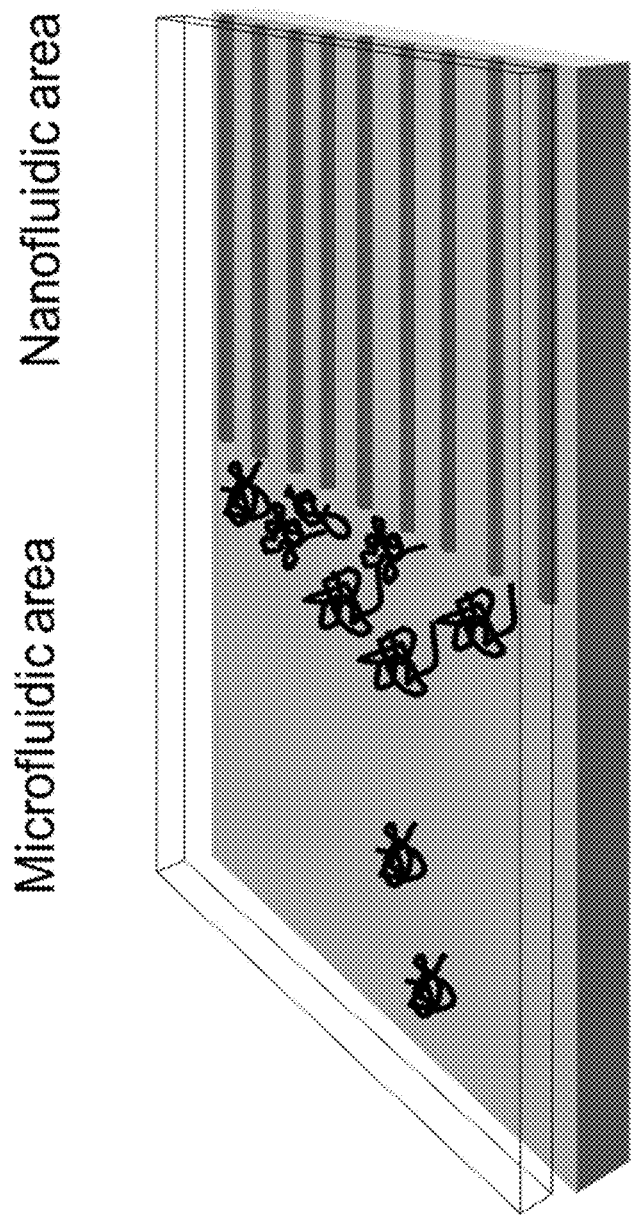
FIG. 1A is a schematic diagram of a prior art device including nanochannels.

Reference will now be made in greater detail to a preferred embodiment of the invention, an example of which is illustrated in the accompanying drawings. Wherever possible, the same reference numerals will be used throughout the drawings and the description to refer to the same or like parts.

Figure 2:
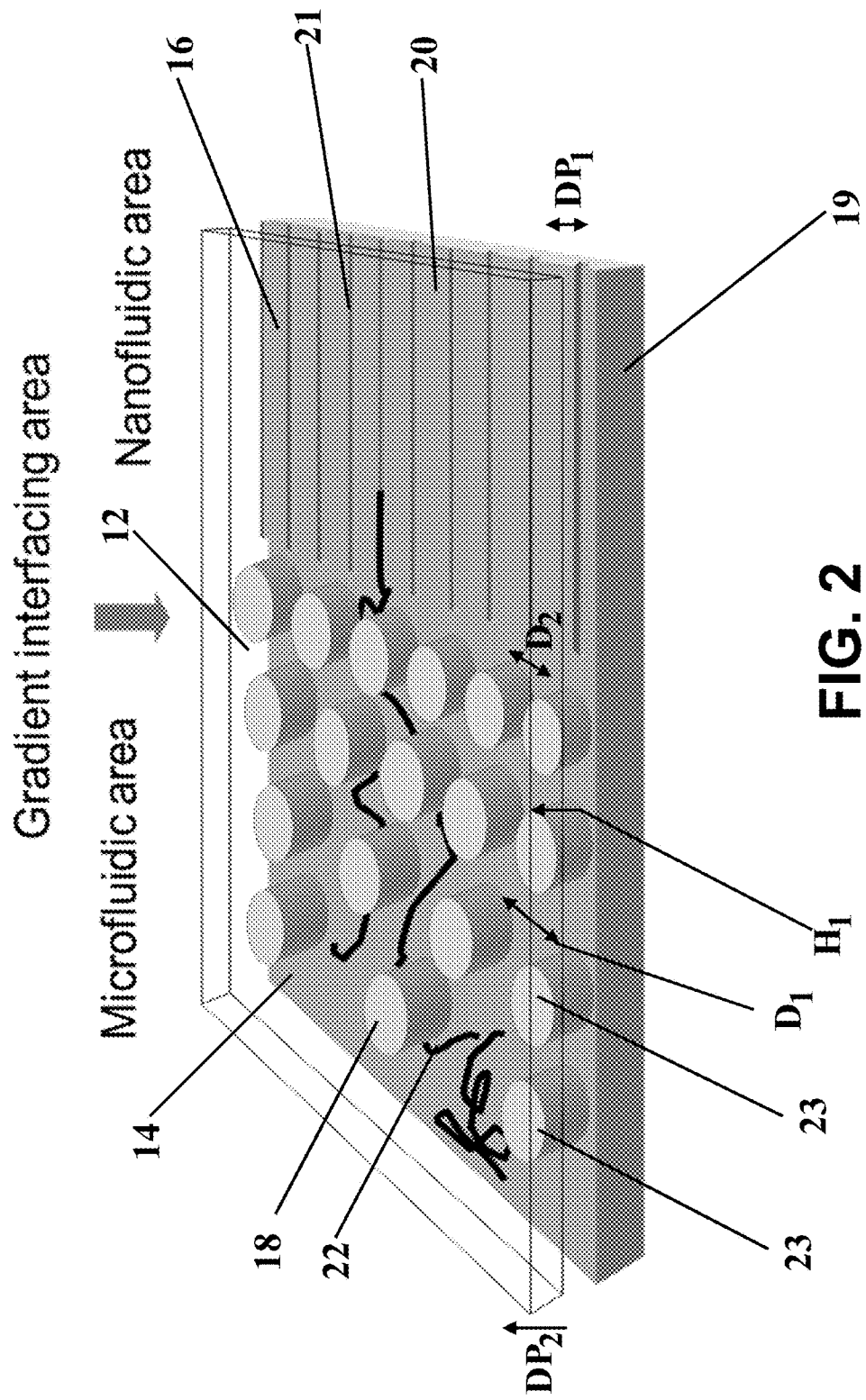
FIG. 2 is a schematic diagram of a device for interfacing microfluidic and nanofluidic components in accordance with the teachings of the present invention.

FIG. 2 is a schematic diagram of device 10 for interfacing microfluidic and nanofluidic components in accordance with the teachings of the present invention. Gradient interface area 12 is positioned between microfluidic area 14 and nanofluidic area 16. Microfluidic area 14 can comprise a plurality of microposts 18 formed on substrate 19. For example, microposts 18 can have a diameter in the range of about 0.5 to about 5.0 microns and distance $D_1$ between microposts 18 can be in the range of about 0.5 to about 5.0 microns. In one embodiment, microposts 18 have a diameter in the range of about 1.2 to about 1.4 microns and a distance $D_1$ between microposts 18 in a range of about 1.5 to about 2.0 microns.

Nanofluidic area 16 can comprise a plurality of nanochannel arrays 20 including a surface having a plurality of nanochannels 21 in the material of the surface. By "a plurality of channels" is meant more than two channels, typically more than 5, and even typically more than 10, 96, 100, 384, 1,000, 1,536, 10,000, 100,000 and 1,000,000 channels. Nanochannels 21 can be provided as a plurality of parallel linear channels across substrate 19. Nanochannels 21 can have a trench width of less than about 150 nanometers, more typically less than 100 nanometers, and even more typically less than: 75, 50, 25 and 15 nanometers. In certain embodiments, the trench width can be about 10 nanometers. In the present invention, the trench width can be at least 2 nm, and typically at least 5 nm. Nanochannels 21 can have a trench depth of less than about 200 nanometers.

The nanochannels can have sealing material adjacent to the channel wall material. In this embodiment, the sealing material can reduce the trench width. Varying the sealing material deposition parameters can be used to narrow the trench width of the channels. The deposition parameters can be varied to provide trench widths of typically less than 100 nanometers. As more material is deposited, trench widths can be narrowed to less than 75 nanometers, and even less than: 50 nanometers, 25 nanometers, and 15 nanometers. Trench widths of about 10 nm can also be provided by the methods of the present invention. Typically, the resulting trench widths after deposition will be greater than 2 nm, and more typically greater than 5 nanometers. Trench depths of less than 175, 150, 125, 100, 75, 50, and 25 nm can also be provided by the methods of the present invention. Trench depths of about 15 nm can also be provided. Typically, the trench depths will be at least 5 nm, and more typically at least 10 nm.

In certain embodiments, the trench depth is typically less than 175 nm, and more typically less than 150 nm, 125 nm, 100 nm, 75 nm, 50 nm and 25 nm. In certain embodiments, the trench depth is about 15 nm. In certain embodiments, the trench depth is at least 2 nm, typically at least 5 nm, and more typically at least 10 nm. At least some of the nanochannels 21 can be surmounted by sealing material to render such channels at least substantially enclosed. The lengths of the channels of the nanochannel array can have a wide range.

The lengths of the channels can also be the same or different in nanochannel array 20. For carrying out macromolecular analysis using nanochannel array 20 as provided below, it is desirable that nanochannels 21 are at least about 1 millimeter (mm), 1 micrometer (μm) or longer. The length of nanochannels 21 is greater than about 1 millimeter (mm), about 1 centimeter (cm), and even greater than about 5 cm, about 15 cm, and about 25 cm. Nanochannels 21 can be fabricated with nanoimprint lithography (NIL), as described in Z. N. Yu, P. Deshpande, W. Wu, J. Wang and S. Y. Chou, Appl. Phys. Lett. 77 (7), 927 (2000); S. Y. Chou, P. R. Krauss, and P. J. Renstrom, Appl. Phys. Lett. 67 (21), 3114 (1995); Stephen Y. Chou, Peter R. Krauss and Preston J. Renstrom, Science 272, 85 (1996) and U.S. Pat. No. 5,772,905 hereby each incorporated in their entirety by reference into this application. Nanochannel 21 can be formed by nanoimprint lithography, interference lithography, self-assembled copolymer pattern transfer, spin coating, electron beam lithography, focused ion beam milling, photolithography, reactive ion-etching, wet-etching, plasma-enhanced chemical vapor deposition, electron beam evaporation, sputter deposition, and combinations thereof. Alternatively, other conventional methods can be used to form nanochannels.

In an alternate embodiment, nanofluidic area 16 can comprise nanoscale fluidic structures. For example, the nanoscale fluidic structures can comprise nanopillars and nanospheres.

Figure 3:
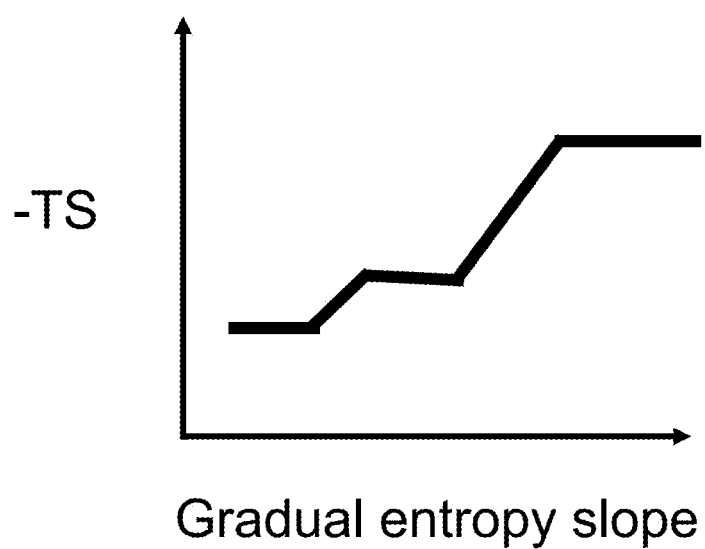
FIG. 3 is a graph of entropy change to the nanochannels of the device of FIG. 2.

Gradient interface area 12 is used to effectively stretch and align biopolymers 22 before they approach nanofluidic area 16. Biopolymers 22 can be preliminarily stretched between adjacent pairs of microposts 18 before entering nanochannels 21. Gradient interface area 12 reduces the steepness of the entrophy barrier before biopolymers 22 enter nanofluidic area 16, as shown in FIG. 3.

Referring to FIG. 2, gradient interface area 12 can comprise a plurality of gradient structures 23 formed on substrate 19. Distance $D_2$ between gradient structures 23 is gradually reduced towards nanofluidic area 16. For example, distance $D_2$ between gradient structures 23 can be reduced from about 2 microns to gradually below about 500 nm, about 400 nm, about 200 nm, about 150 nm, about 10 nm, about 5 nm and about 2 nm. In one embodiment, the distance $D_2$ between gradient structures 23 is reduced in a range of about a radius of gyration of biopolymer 22 to substantially a diameter of biopolymer 22. For example, diameter $D_2$ between gradient structures 23 can be reduced in the range of about 2 nm, a diameter of a DNA module, to about 700 nm, a radius of gyration of a T4 phage DNA molecule.

Gradient structures 23 can provide a gradual elevation of height $H_1$ from substrate 19. Nanofluidic area 16 can have a shallower depth $DP_1$ than depth $DP_2$ of microfluidic area 14. Accordingly, gradual elevation of height $H_1$ from microfluidic area 14 to nanofluidic area 16 provides improved interconnection of microfluidic area 14 with nanofluidic area 16.

Figure 4B:
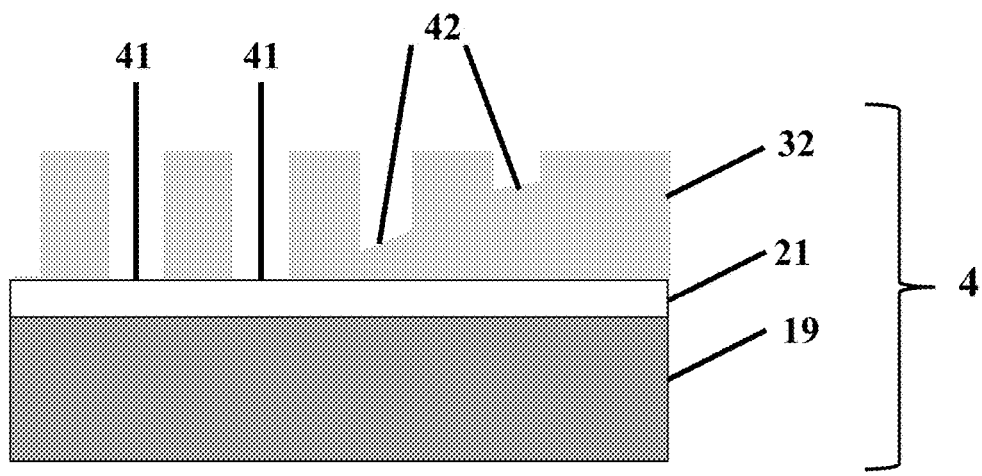
Figure 4C:
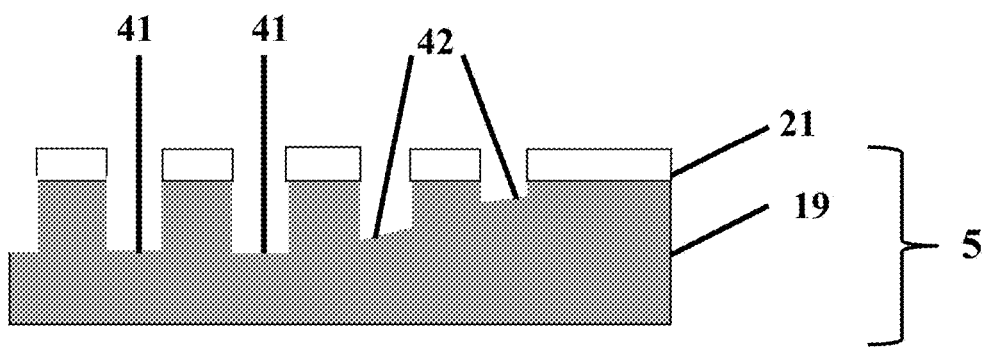

Basic fabrication steps of the present invention using diffraction gradient lithography are outlined in partial, schematic perspective views in FIGS. 4A-4C, as including processing steps 1-3. One or more nanochannels 21 were fabricated on substrate 19 in this process. Substrate 19 can be a silicon wafer substrate. Alternatively, any type of material compatible with the photolithography can be used as a substrate. Substrate 19 was coated with photoresist 32 after HMDS treatment and baked. Photomask 34 having a micron size post array can be used to pattern microfluidic area 14 and gradient interface area 12, in step 1.

In step 2, blocking mask 35 was placed over or coated on photomask 34. Blocking mask 35 extends over portion 36 of photomask 34. Blocking mask 35 masks portion 38 of nanofluidic area 16 positioned under portion 36 of photomask 34 to protect nanochannels 21. In step 3, device 10 was exposed to incident UV light 37. Blocking mask 35 causes light diffraction along edge 39 of blocking mask 35.

Blocking mask 35 can be formed of any material which is opaque to exposing light used in optical lithography. For example, blocking mask 35 can be formed of a metal, such as aluminum foil or an opaque plastic.

Referring to FIG. 4B, in step 4, device 10 was developed using conventional techniques. Light diffraction caused by edge 39 of blocking mask 35 generates a gradient in dissolution rate of photoresist 32 by the developer. During development, exposed photoresist 32 was completely removed at portion 41 which is not blocked by blocking mask 35, exposing the substrate surface underneath. At portion 42, photoresist 32 has a gradient of undeveloped photoresist along the light diffraction area. The thickness of the gradient of undeveloped photoresist corresponds to exposure to diffracted light. At portion 43, blocking mask 35 completely blocks exposure of photoresist 32 to light.

Referring to FIG. 4C, in step 5, photoresist 32 was used as an etching mask during a reactive ion etching (RIE) process and gradient patterns in photoresist 32 were transferred into substrate 19.

Figure 4D:
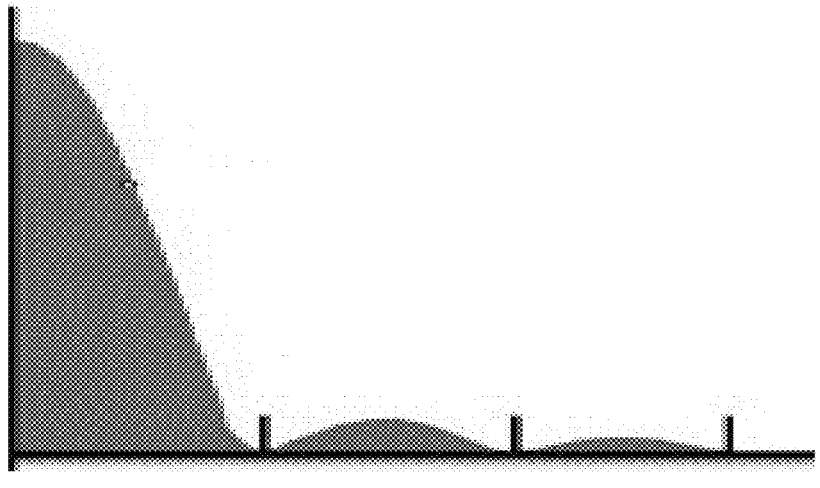

A light intensity profile on photomask 34 is shown in FIG. 4D. The light intensity profile shows reduced light intensity along edge 39 of blocking mask 35. The gradient profile can be controlled by the type of photoresist, development conditions and etching conditions. For example, a low contrast resist can provide a gradual gradient profile. Edge 39 of blocking mask 35 can be varied to adjust the gradient profile. For example, edge 39 can be angled or patterned to adjust the gradient profile.

Figure 5A:
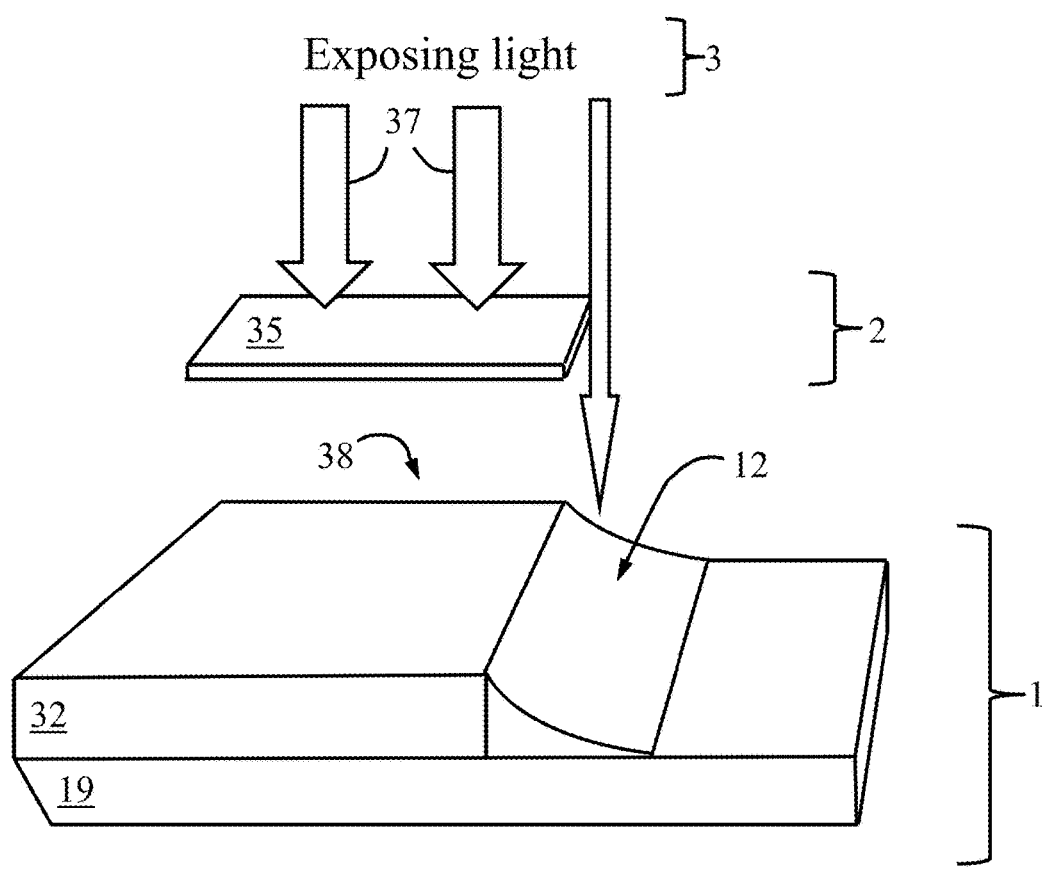
FIGS. 5A-5B diagrammatically illustrate a process incorporating diffraction gradient lithography (DGL) to fabricate a sloped gradient interface area.
Figure 5B:
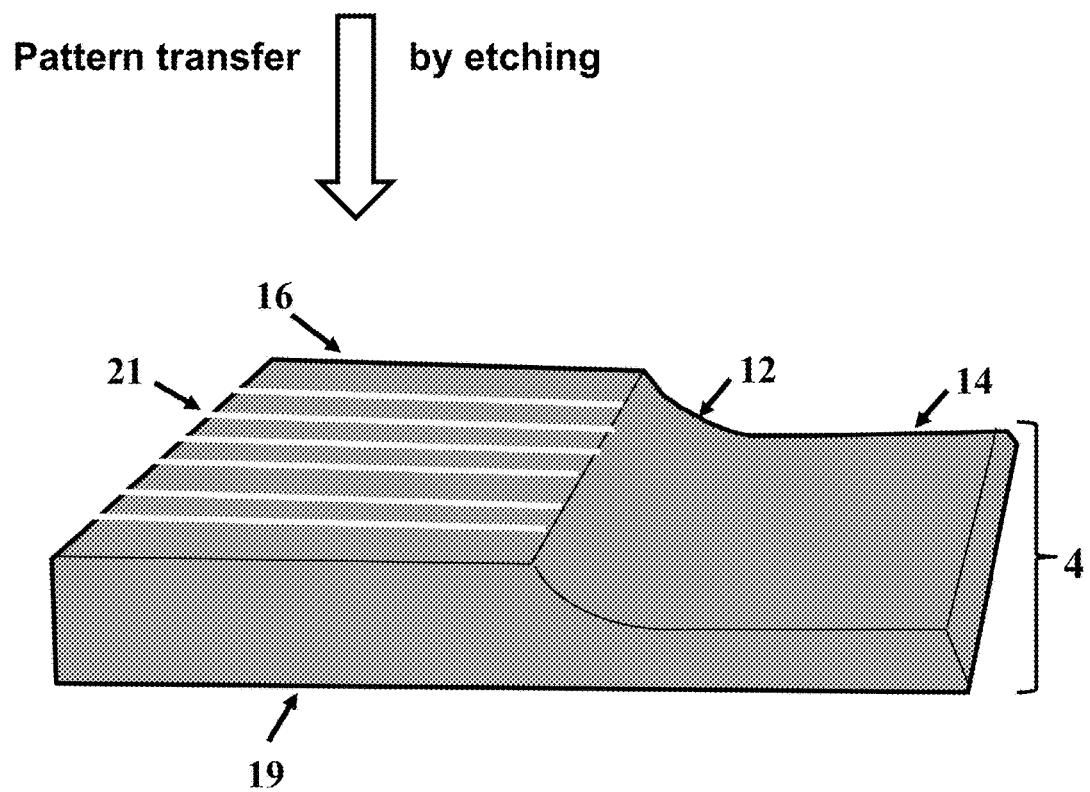

In one embodiment, gradient interface area 12 is formed as a gradual slope from microfluidic area 14 to nanofluidic area 16, as shown in FIGS. 5A-5B. In this embodiment, one or more nanochannels were fabricated in substrate 19. Substrate 19 was coated with photoresist 32 after HMDS treatment and baked, in step 1. In step 2, blocking mask 35 was placed over photoresist 32. Blocking mask 35 extends over portion 36 of photomask 34. Blocking mask 35 masks portion 38 of nanofluidic area 16 to protect nanochannels 21. In step 3, device 10 was exposed to incident UV light 37. Blocking mask 35 causes light diffraction along edge 39 of blocking mask 35. In step 4, device 10 was developed using conventional techniques. Photoresist 32 was used as an etching mask during a reactive ion etching (RIE) process and gradient patterns in photoresist 32 were transferred into substrate 19. During development, the diminishing light intensity casted on photoresist 32 forms a gradient vertical slope in gradient interface area 12 which is transferred into substrate 16.

Figure 6A:
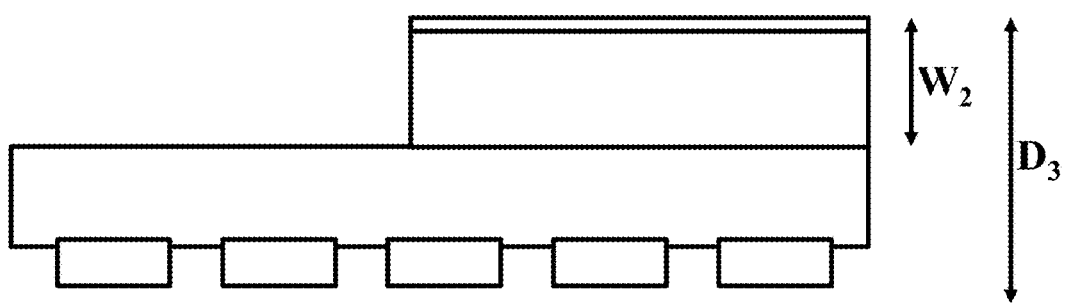
FIG. 6A is a schematic diagram of a method for adjusting the diffraction gradient using thickness.
Figure 6B:
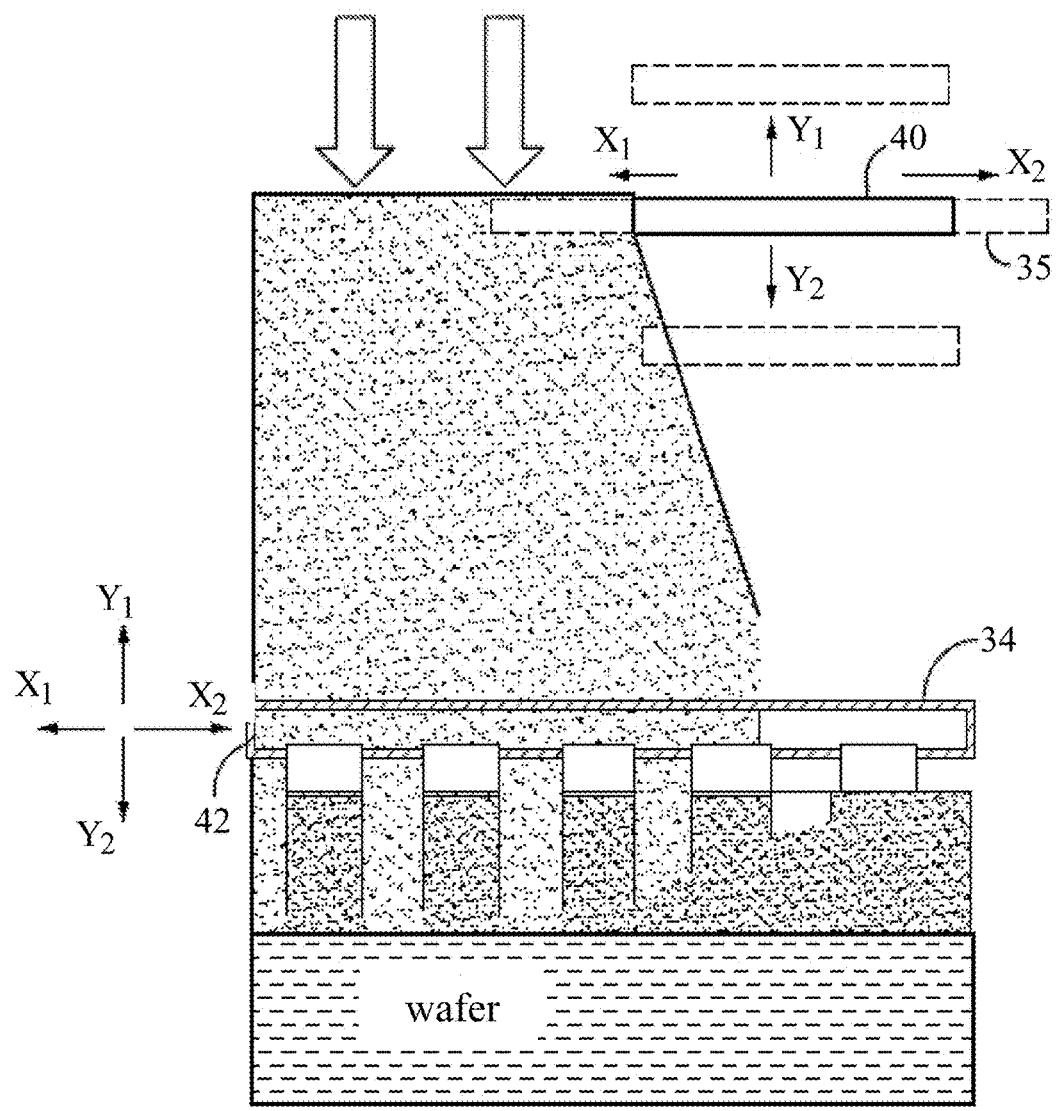
FIG. 6B is a schematic diagram of a method for adjusting the diffraction gradient using a variable distance.

Width $W_2$ of blocking mask 35 and distance between photomask 34 and blocking mask 35 can be varied to determine the distance $D_3$ of blocking mask 35 to photoresist 32, as shown in FIGS. 6A-6B. For example, blocking mask 35 can have a varying width $W_2$ in the range of about 1 mm to about 10 mm. $W_2$ can be formed of one or more additional blocking masks which are fused to blocking mask 35 for increasing Width $W_2$ of blocking mask 35. Blocking mask 35 can be coated on photomask 34.

In an alternate embodiment, distance $D_3$ of blocking mask 35 to photoresist 32 can be adjusted by adjusting the distance between blocking mask 35 and photomask 34. Blocking mask 35 can be positioned over photomask 34 using blocking mask holder 40. Photomask 34 can be positioned over photoresist 32 using aligner 42. Blocking mask holder 40 can move blocking mask in $X_1$, $X_2$, $Y_1$, $Y_2$ directions. Aligner 42 can move photomask 34 in the $X_1$, $X_2$, $Y_1$, $Y_2$ directions. Distance $D_3$ can be varied upon movement of blocking mask 35 towards and away from photoresist 32. Distance $D_3$ determines diffraction to photoresist 32. For example, a smaller distance $D_3$ provides a narrower diffraction zone in gradient interface area 12.

Figure 7:
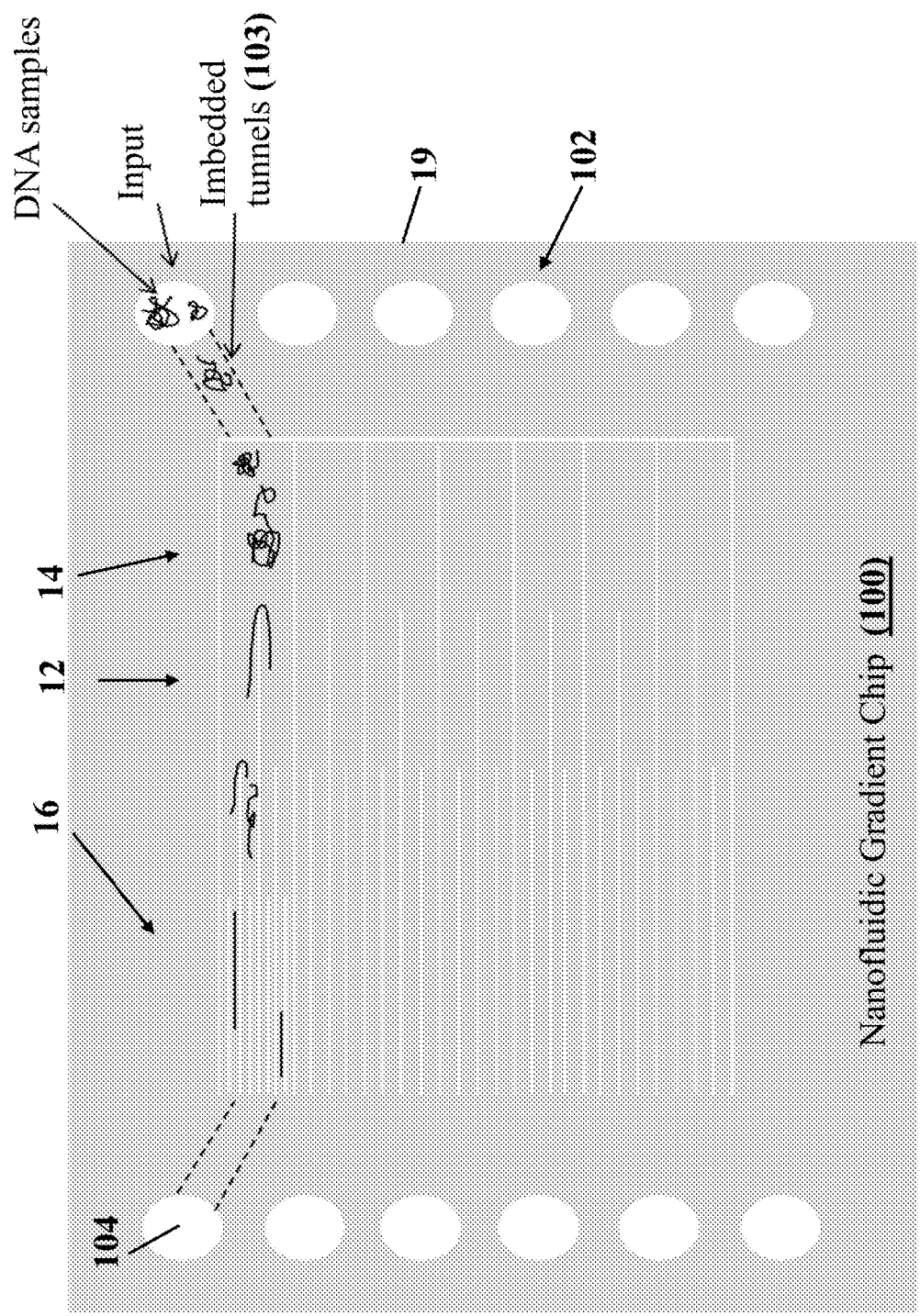
FIG. 7 is a schematic diagram of a microfluidic/nanofluidic chip.

In another aspect of the invention, there is provided a microfluidic/nanofluidic chip that includes the gradient interface area for interfacing microfluidic and nanofluidic components. Referring to FIG. 7, microfluidic/nanofluidic chip 100 has microfluidic area 14, substrate 19, nanofluidic area 16, gradient interface area 12 and reservoirs 102 for handling samples and reservoirs 104 for receiving samples and sample collection. Tunnels 103 formed in substrate 19 can be used for connecting reservoirs 102 and 104 respectively to microfluidic area 14 and nanofluidic area 16.

Nanofluidic area 16 can comprise nanofluidic channels 21 as described above. Alternatively, nanofluidic area 16 and gradient interface area 12 can comprise branched channels 106. Branched channels 106 can be split into smaller and smaller branches range from about 5.0 microns to about 2 nanometers to provide decreasing lateral gradient distances between channels providing a lateral gradient. Branched channels 106 can include a gradual elevation in height formed using diffraction gradient lithography, as described above.

The reservoirs are in fluid communication with at least one of the channels, so that the sample reservoirs are capable of releasing a fluid into the channels, and the waste reservoirs are capable of receiving a fluid from the channels. Typically the fluids contain macromolecules for analysis.

In certain embodiments of the present invention, the microfluidic/nanofluidic chip contains at least one sample reservoir formed in the surface of the substrate. Reservoirs can be defined using photolithography and subsequently pattern transferred to the substrate using Reactive Ion etching (RIE), chemical etching or FIB milling directly to create reservoirs in fluid communication with nanofluidic area 16 or nanochannels 21. In this embodiment, at least one waste reservoir in fluid communication with at least one of the channels. Typically, the microfluidic/nanofluidic chip contains at least 1 sample reservoir. Alternatively, a variety of other embodiments include various numbers of reservoirs.

For use in macromolecular analysis, microfluidic/nanofluidic chip 100 can provide at least a portion of nanofluidic area 16 capable of being imaged with a two-dimensional detector. Imaging of the nanofluidic area 16 is provided by presenting the nanochannels and any sealing material to suitable apparatus for the collection of emitted signals, such as optical elements for the collection of light from the nanochannels. In this embodiment, the microfluidic/nanofluidic chip is capable of transporting a plurality of elongated macromolecules from a sample reservoir, across macrofluidic area and across the nanofluidic area.

In certain embodiments of the present invention, the microfluidic/nanofluidic chip contains an apparatus for transporting macromolecules from the sample reservoirs, through the macrofluidic area, nanofluidic area, and into the waste reservoirs. A suitable apparatus includes at least one pair of electrodes capable of applying an electric field across at least some of the channels in at least one direction. Electrode metal contacts can be integrated using standard integrated circuit fabrication technology to be in contact with at least one sample and at least one collection/waste reservoir to establish directional electric field. Alternating current (AC), direct current (DC), or both types of fields can be applied. The electrodes can be made of almost any metal, and are typically thin Al/Au metal layers deposited on defined line paths. Typically at least one end of one electrode is in contact with buffer solution in the reservoir.

In certain embodiments of the present invention, the microfluidic/nanofluidic chip contains at least two pair of electrodes, each providing an electric field in different directions. With at least two sets of independent electrodes, field contacts can be used to independently modulate the direction and amplitudes of the electric fields to move macromolecules at desired speed or directions.

Figure 8:
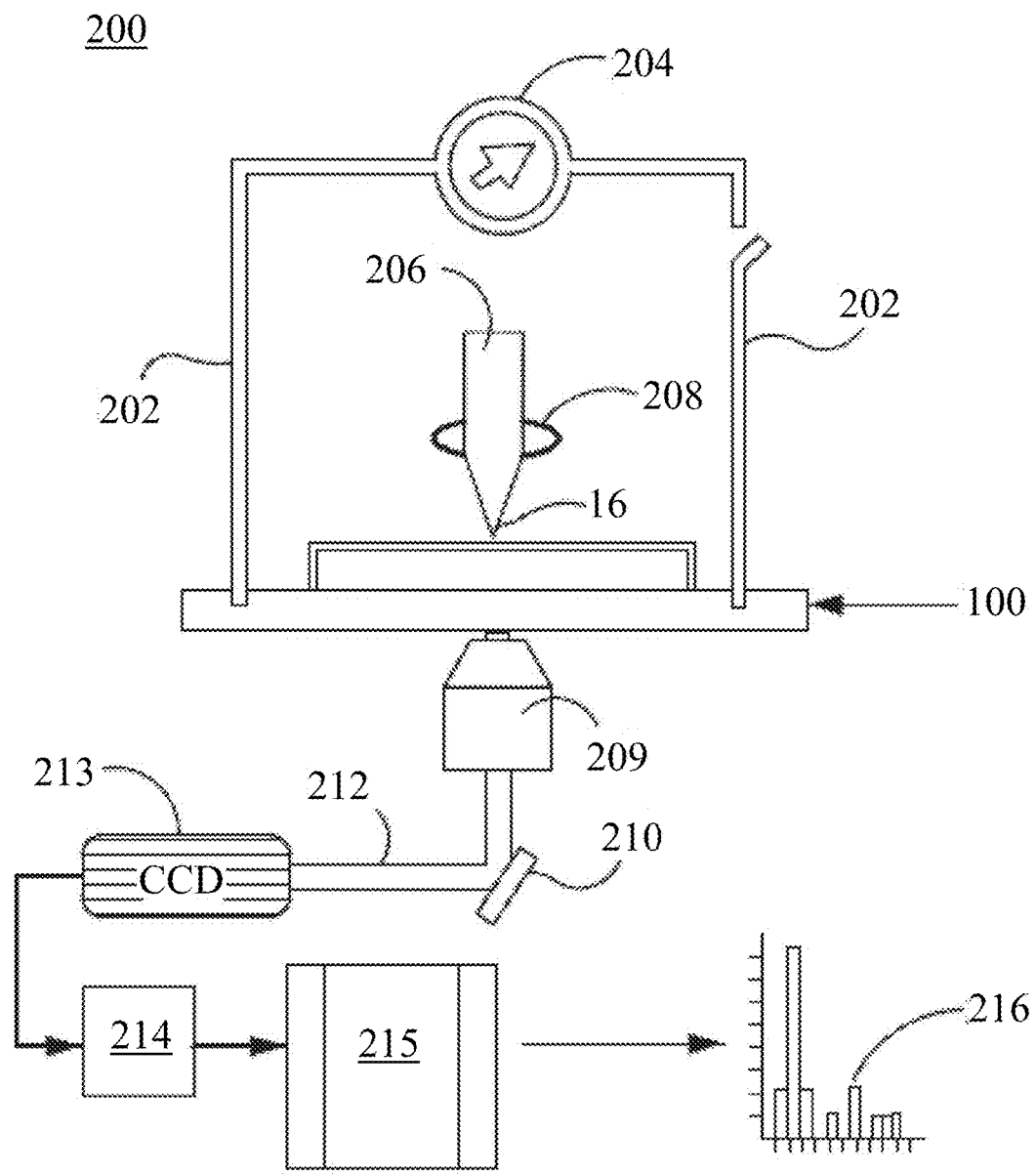
FIG. 8 is a schematic diagram of a system for analyzing macromolecules using the microfluidic/nanofluidic chip.

In another aspect of the present invention, system 200 is used for carrying out macromolecular analysis, as shown in FIG. 8. System 200 includes a microfluidic/nanofluidic chip 100 as described herein, and an apparatus for detecting at least one signal transmitted from one or more fluids in nanochannels 21 of the microfluidic/nanofluidic chip 100.

In various embodiments of the present invention, the system further includes at least one of the following: a transporting apparatus to transport a fluid through at least microfluidic area 14 and nanochannels 21; a sample loading apparatus for loading at least one fluid to sample reservoirs in microfluidic/nanofluidic chip 100; image or signal detectors and a data processor.

Microfluidic/nanofluidic chip 100 used in system 200 is typically disposable, individually packaged, and having a sample loading capacity of 1-50,000 individual fluid samples. Microfluidic/nanofluidic chip 100 typically has sample loading openings and a reservoir, or sample loading openings and plates connected with a sealing mechanism, such as an O-ring. Electrodes 202 are connected to electric potential generator 204 and microfluidic/nanofluidic chip 100. Electrodes 202 and electric potential generator 204 can be connected with metal contacts. Suitable metal contacts can be external contact patches that can be connected to an external scanning/imaging/electric-field tuner.

In one embodiment of the present invention, system 200 includes an apparatus to excite the macromolecules inside the channels and detect and collect the resulting signals. Laser beam 206 is focused using a focusing lens 208 to a spot on nanofluidic area 16. The generated light signal from the macromolecules inside the nanofluidic area or nanochannels (not shown) is collected by focusing/collection lens 209, and is reflected off a dichroic mirror/band pass filter 210 into optical path 212, which is fed into CCD (charge coupled device) camera 213. Alternatively, exciting light source could be passed through a dichroic mirror/band pass filter box, 210 and focusing/collecting scheme from the top of the chip. Various optical components and devices can also be used in the system to detect optical signals, such as digital cameras, PMTs (photomultiplier tubes), and APDs (Avalanche photodiodes).

System 200 can include data processor 214. Data processor 214 can be used to process the signals from CCD 213 to project the digital image of nanofluidic area 16 on display 215. Data processor 214 can also analyze the digital image to provide characterization information, such as macromolecular size statistics, histograms, karyotypes, mapping, diagnostics information and display the information in suitable form for data readout 216.

Microfluidic/nanofluidic chip 100 can be encased in a suitable housing, such as plastic, to provide a convenient and commercially-ready cartridge or cassette. Typically the nanofluidic cartridges will have suitable features on or in the housing for inserting, guiding, and aligning the sample loading device with the reservoirs. Insertion slots, tracks, or both can be provided in the plastic case.

Macromolecular fluid samples that can be analyzed by the system includes fluids from a mammal (e.g., DNA, cells, blood, Serum, biopsy tissues), synthetic macromolecules such as polymers, and materials found in nature (e.g., materials derived from plants, animals, and other life forms). Such fluid samples can be managed, loaded, and injected using automated or manual sample loading apparatus of the present invention.

In another aspect of the present invention, there is provided a method of analyzing at least one macromolecule. In this invention, the analysis includes the steps of providing a microfluidic/nanofluidic chip 100 according to the present invention, providing the at least one sample reservoir with at least one fluid, the fluid comprising at least one macromolecule; transporting the at least one macromolecule from a macrofluidic area through a gradient interface area into the at least one channel to elongate said at least one macromolecule; detecting at least one signal transmitted from the at least one elongated macromolecule; and correlating the detected signal to at least one property of the at least one macromolecule.

In one embodiment of the present invention, the method of analyzing a macromolecule includes wetting the channels using capillary action with a buffer solution or a buffer solution containing macromolecules. Macromolecules such as polymers and DNA can be introduced into nanochannel arrays by electric field, capillary action, differential surface tension by temperature or chemical gradient or differential pressure such as vacuum.

Various macromolecules can be analyzed using the present method. For analyzing DNA typical process conditions include providing dilute solutions of DNA which are stained at a ratio of 4:1 to 10:1 base pair/dye with a suitable dye. Suitable dye stains include TOTO-1, BOBO-1, BOBO-3 (Molecular Probes, Eugene, Oreg.). Solutions of stained DNA can be further diluted and treated with an anti-oxidant and an anti-sticking agent.

In one embodiment of the present invention, the method of analyzing a macromolecule includes the sizing of one DNA macromolecule. One DNA macromolecule can be extracted from a single cell or spore, such as anthrax, and suitably transported (e.g., in a polymerized gel plugs) to avoid breakage.

The length of a single DNA can be detected/reported and intensity profile can be plotted. In various embodiments of the present invention, the method of analyzing a macromolecule includes correlating the detected signal to at least one of the following properties: length, conformation, and chemical composition. Various macromolecules that can be analyzed this way include, biopolymers such as a protein, a polypeptide, and a nucleic acid such as RNA or DNA or PNA. For DNA nucleic acids, the detected signals can be correlated to the base pair sequence of said DNA.

The typical concentration of the macromolecules in the fluid will be one macromolecule, or about at least attogram per ml, more typically at least one femtogram per ml, more typically at least one picogram per ml, and even more typically at least one nanogram per ml. Concentrations will typically be less than about 5 micrograms per milliliter and more typically less than about 0.5 micrograms per milliliter.

In one embodiment of the present invention, the method of analyzing a macromolecule measures the length of macromolecules having an elongated length of greater than 150 nanometers, and typically greater than about 500 nanometers, about 1 micron, about 10 microns, about 100 microns, about 1 mm, about 1 cm, and about 10 cm long.

DNA having greater than 10 base pairs can also be analyzed using the present methods. Typically, the number of base pairs measured can be greater than 100 base pairs, greater than 1,000 base pairs, greater than 10,000 base pairs, greater than 100,000 base pairs and greater than 1,000,000 base pairs. DNA having more than 1 million, 10 million, and even 100 million basepairs can be analyzed with the present methods.

In one embodiment of the present invention, the methods can be used to analyze one or more of the following: restriction fragment length polymorphism, a chromosome, and single nucleotide polymorphism.

The invention can be further illustrated by the following examples thereof, although it will be understood that these examples are included merely for purposes of illustration and are not intended to limit the scope of the invention unless otherwise specifically indicated. All percentages, ratios, and parts herein, in the Specification, Examples, and claims, are by weight and are approximations unless otherwise stated.

EXAMPLES

Large arrays of nanochannels were first fabricated on an entire Si substrate chip using nanoimprinting lithography, described in S. Y, Chou, P. R. Krauss, and P. J. Renstrom, Appl. Phys. Lett. 67 (21), 3114 (1995); Stephen Y. Chou, Peter R. Krauss and Preston J. Renstrom, Science 272, 85 (1996) and U.S. Pat. No. 5,772,905. This chip was spin coated with positive tone photoresist (AZ5214-E) using standard protocol at 4000 rpm for 1 min after HMDS treatment and baked at 110° C. for 2 min. A Karl Suss MA-6 contact aligner and a uniform micron feature size hexagon array photomask were used to pattern the microfluidic area. A blocking mask of a piece of aluminum foil was placed on top of the photomask. The distance between the blocking mask and the photoresist surface was about 3 mm. The chip was exposed at 400 nm UV light in hard contact mode for 35 seconds and developed with a standard procedure (AZ312 MIF:$H_2O$ 1:1). The photoresist was used as an etching mask during a subsequent reactive ion etching (RIE) process and the gradient patterns in the photoresist were transferred into the underlying Si substrate.

Figure 9A:
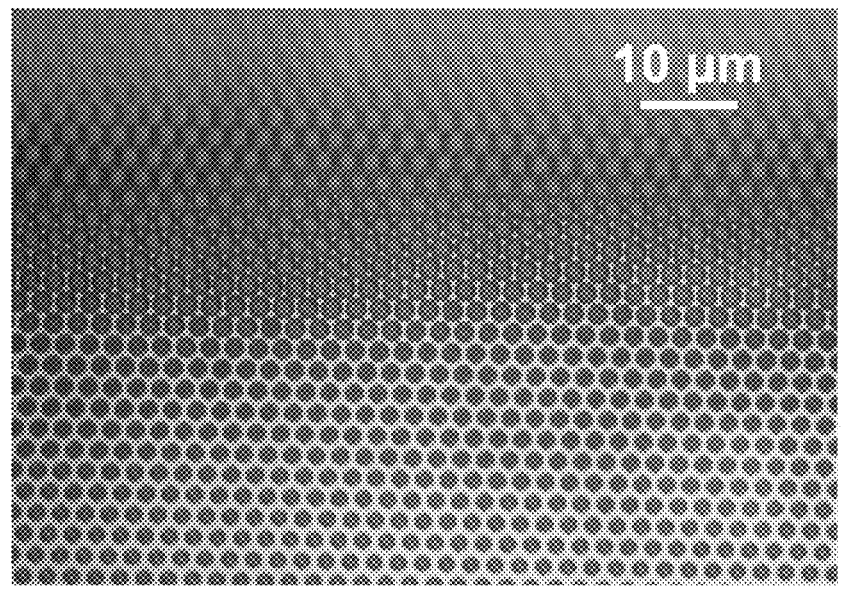
FIG. 9A is an optical image during fabrication of the device of the present invention after photoresist development, in accordance with FIG. 4B, step 4.
Figure 9B:
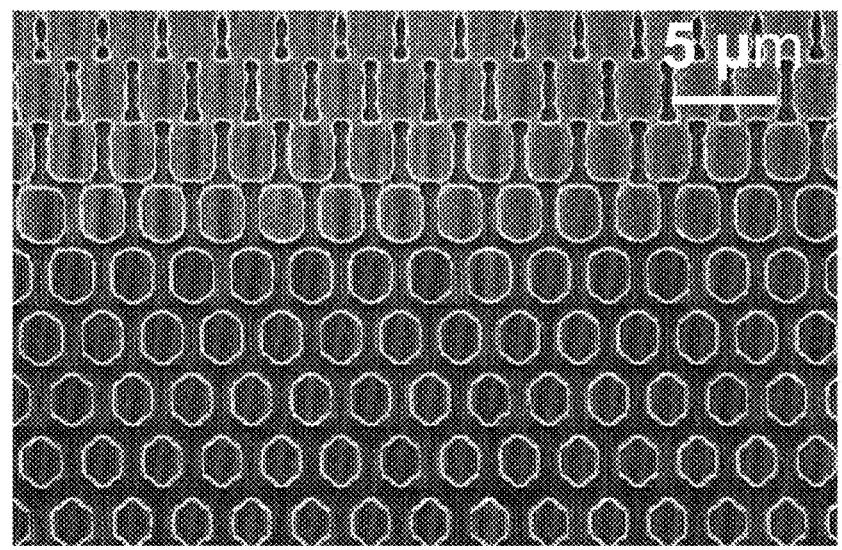
FIG. 9B is a scanning electronic microscope during fabrication of the device of the present invention after pattern transfer and photoresist removal, in accordance with FIG. 4C, step 5.

FIG. 9A shows a top view optical image of the actual gradient chip after photoresist development. The gaps between posts were then etched into the chip using a combination of $O_2$ and $CHF_3$ plasma followed by removal of the resist using acetone. FIG. 9B shows a scanning electronic microscope (SEM) image of the interfacing zone with gradient lateral spacing between microposts after pattern transfer and photoresist removal. The area directly under the blocking mask with the prefabricated nanochannels is protected from RIE by the masking photoresist.

Figure 10A:
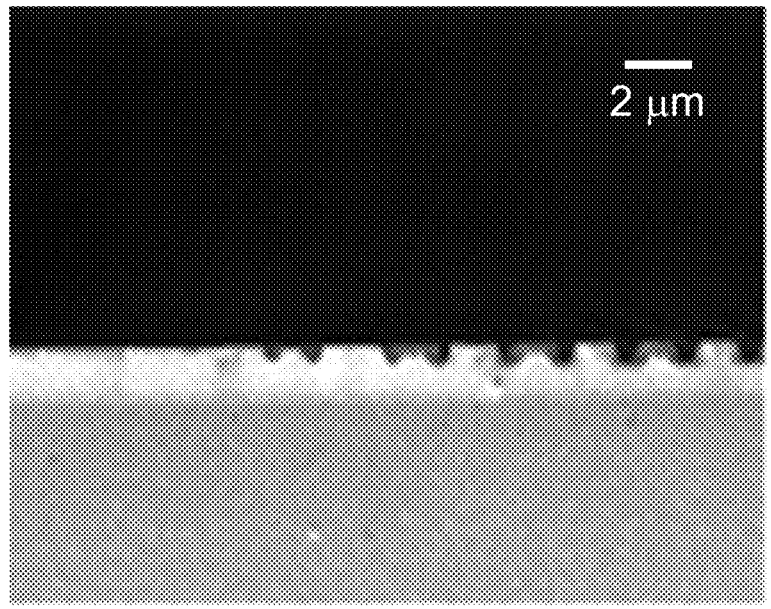
FIG. 10A is a scanning electronic microscope during fabrication of the device of the present invention after pattern transfer and photoresist removal using a first etching condition, in accordance with FIG. 4C, step 5.
Figure 10B:
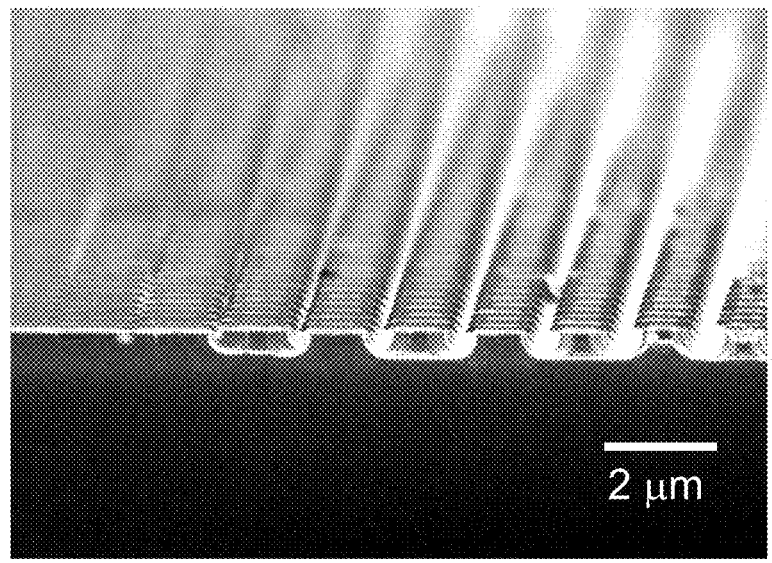
FIG. 10B is a scanning electronic microscope during fabrication of the device of the present invention after pattern transfer and photoresist removal using a second etching condition, in accordance with FIG. 4C, step 5.

FIGS. 10A-10B illustrate cleaved profile SEM images showing the gradual reduction of the gaps between the microposts, typically from 1.2 μm gradually to below 400 nm, and the gradual elevation of the substrate of the fluidic chip to interconnect to the shallower nanofluidic channels. The gradient profile shown in FIGS. 10A and 10B is slight differently controlled by the choice of photoresist, development and etching conditions.

Figure 1B:
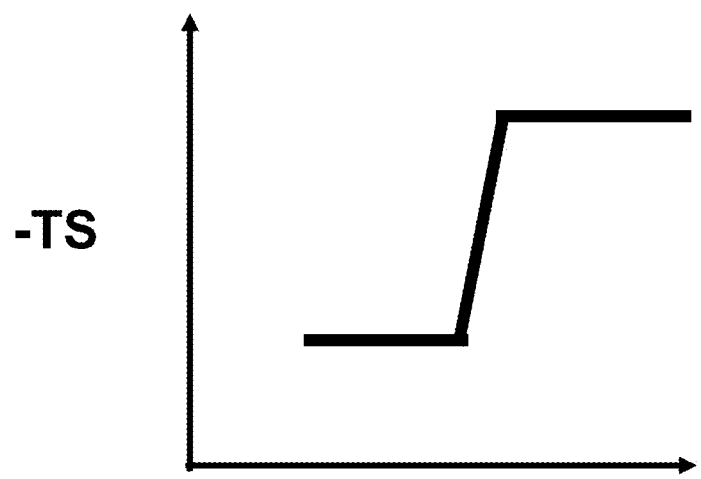
FIG. 1B is a graph of entropy change to the nanochannels of the device of FIG. 1A.
Figure 11A:
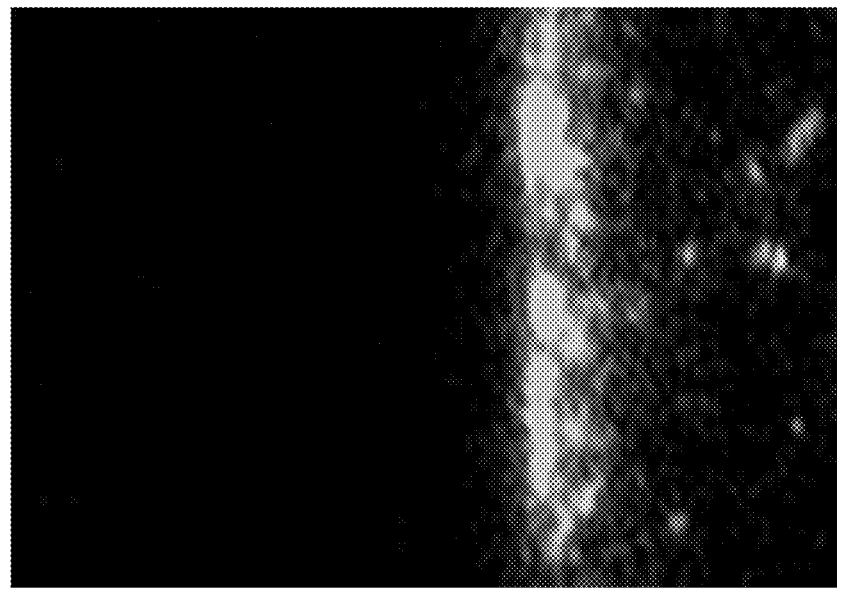
FIG. 11A is an intensified charge coupled device (CCD) image of fluorescent long DNA molecules entering the prior art nanofluidic chip shown in FIG. 1.
Figure 11B:
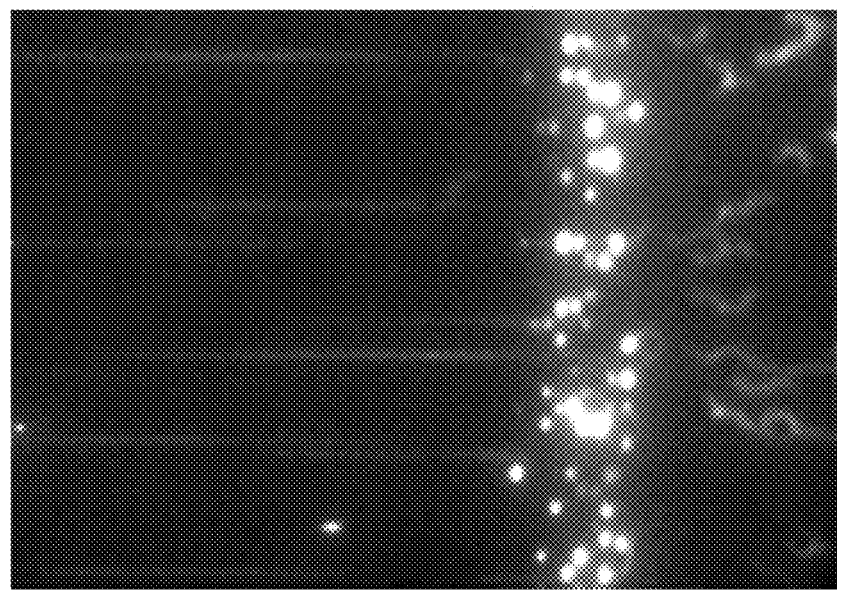
FIG. 11B is an intensified charge coupled device (CCD) image of fluorescent long DNA molecules entering device 10 shown in FIG. 2.

Fluorescently stained long DNA molecules were introduced into prior art nanofluidic chips shown in FIG. 1 and device 10 shown in FIG. 2. In FIG. 11A, DNA entered from the right side of the image, and approached and stalled at the edge of the prior art nanofluidic chip, causing fouling of the chip. In FIG. 11B, lambda phage DNA molecules or genomic BAC DNA were partially uncoiled when they entered the gradient area, and slowed down at the edge of the nanochannels due to "uphill" entrophy. Larger DNA molecules moved into the nanochannels continuously and remained stretched, with significantly improved efficiency. Moving DNA molecules can be seen in the left part of the image as long white streaks after image integration.

It is to be understood that the above-described embodiments are illustrative of only a few of the many possible specific embodiments which can represent applications of the principles of the invention. Numerous and varied other arrangements can be readily devised in accordance with these principles by those skilled in the art without departing from the spirit and scope of the invention.

What is claimed:

1. A method of analyzing at least one macromolecule, comprising the steps of:
    providing a surface having
        a nanofluidic area formed of at least one channel in the material of the surface;
        a microfluidic area on said surface; and
        a gradient interface area between said nanofluidic area and said microfluidic area;
    introducing a sample into the microfluidic area, said sample comprising at least one macromolecule;
    transporting the at least one macromolecule between said microfluidic area and said nanofluidic area to elongate said at least one macromolecule;
    detecting at least one signal transmitted from the at least one elongated macromolecule; and
    correlating the at least one detected signal to at least one property of the at least one macromolecule.

2. The method according to claim 1 wherein the detected signal is correlated to at least one property selected from the group consisting of length, conformation, attachment and chemical composition.

3. The method according to claim 1 wherein the macromolecule is a synthetic polymer or biopolymer.

4. The method of claim 3 wherein the biopolymer is at least one of: a protein, a polypeptide, and a nucleic acid.

5. The method of claim 4 wherein the nucleic acid is DNA and the at least one detected signal is correlated to a property of said DNA, wherein the property is selected from the group consisting of the base pair sequence, copy number, structural variation compared to a control DNA, and presence of single nucleotide polymorphism compared to a control DNA.

6. The method of claim 3 wherein the biopolymer is at least substantially unfolded in the nanofluidic area.

7. The method of claim 1 wherein the macromolecule has an elongated length in the nanofluidic area of greater than 150 nanometers.

8. The method of claim 1 wherein the macromolecule is DNA having greater than 100 base pairs.

9. The method of claim 1 wherein the macromolecule is DNA having greater than 1,000 base pairs.

10. The method of claim 1 wherein the macromolecule is DNA having greater than 10,000 base pairs.

11. The method of claim 1 wherein the at least one macromolecule is a chromosome.

12. The method of claim 11 wherein the chromosome is analyzed to determine the presence of at least one single nucleotide polymorphism.

13. A method of detecting a property of at least one macromolecule, comprising the steps of:
    providing a chip that includes at least one nanofluidic structure, a microfluidic area, and a gradient interface area between said at least one nanofluidic structure and said microfluidic area, wherein the gradient interface area has fluidic pathways with cross-sectional areas that generally decrease from the microfluidic area to the at least one nanofluidic structure;
    providing at least one fluid comprising at least one macromolecule to the microfluidic area;
    transporting the at least one macromolecule from said microfluidic area to the at least one nanofluidic structure to elongate said at least one macromolecule; and
    detecting at least one signal indicative of at least one property of the at least one elongated macromolecule.

14. The method according to claim 13 wherein the macromolecule is a synthetic polymer or biopolymer.

15. The method of claim 14 wherein the biopolymer is at least one of: a protein, a polypeptide, and a nucleic acid.

16. The method of claim 15 wherein the nucleic acid is DNA and the detected signal is correlated to a property of said DNA selected from the group consisting of the base pair sequence, copy number, structural variation compared to a control DNA, and presence of single nucleotide polymorphism compared to a control DNA.

17. The method of claim 13 wherein the macromolecule has an elongated length in the at least one nanofluidic structure of greater than 150 nanometers.

18. The method of claim 13 wherein the macromolecule is DNA having greater than 100 base pairs.

19. The method of claim 13, wherein the gradient interface area comprises a plurality of obstacles interposed in a fluid pathway between the microfluidic area and the at least one nanofluidic structure, the obstacles having progressively smaller spacing therebetween along the fluid pathway.

20. A method for analyzing polynucleotide macromolecules, comprising:
providing a device having a nanofluidic area in fluid communication with a microfluidic area, the nanofluidic area comprising at least one nanofluidic channel;
introducing polynucleotide macromolecules into the microfluidic area, where the polynucleotides are at least partially coiled in the microfluidic area;
transporting the polynucleotides through a gradient area linking the microfluidic area and the nanofluidic area, wherein the gradient area includes structure to mechanically elongate the polynucleotides;
transporting the elongated polynucleotides from the gradient area into the at least one nanofluidic channel, wherein the at least one nanofluidic channel has dimensions that maintain the polynucleotides in an elongated form; and
detecting signals indicative of at least one property of the elongated polynucleotides in the at least one nanofluidic channel.

* * * * *